(12) United States Patent
Mitelberg et al.

(10) Patent No.: US 10,426,457 B2
(45) Date of Patent: Oct. 1, 2019

(54) SURGICAL FASTENER DEPLOYMENT SYSTEM

(71) Applicant: Apollo Endosurgery US, Inc., Austin, TX (US)

(72) Inventors: Vladimir Mitelberg, Austin, TX (US); Charles Dean, Austin, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 237 days.

(21) Appl. No.: 15/426,421

(22) Filed: Feb. 7, 2017

(65) Prior Publication Data
US 2018/0221009 A1 Aug. 9, 2018

(51) Int. Cl.
*A61B 17/04* (2006.01)
*A61B 17/10* (2006.01)
*A61F 5/00* (2006.01)
*A61B 17/00* (2006.01)
*A61B 17/06* (2006.01)
*A61B 90/00* (2016.01)

(52) U.S. Cl.
CPC ...... *A61B 17/0401* (2013.01); *A61B 17/0469* (2013.01); *A61F 5/0083* (2013.01); *A61B 2017/00115* (2013.01); *A61B 2017/00292* (2013.01); *A61B 2017/00349* (2013.01); *A61B 2017/00818* (2013.01); *A61B 2017/0409* (2013.01); *A61B 2017/0417* (2013.01); *A61B 2017/0445* (2013.01); *A61B 2017/0464* (2013.01); *A61B 2017/06052* (2013.01); *A61B 2017/06076* (2013.01); *A61B 2090/0803* (2016.02); *A61B 2090/0811* (2016.02)

(58) Field of Classification Search
CPC . A61B 17/10; A61B 17/0401; A61B 17/0469; A61B 2017/0417; A61B 2017/0496; A61B 2017/0412; A61B 2017/0464; A61B 2017/0498
See application file for complete search history.

(56) References Cited

U.S. PATENT DOCUMENTS

| 8,277,468 B2 | 10/2012 | Laufer et al. |
| 2007/0276408 A1 | 11/2007 | Filipi et al. |
| 2015/0250470 A1* | 9/2015 | Vargas ............... A61B 17/0401 606/232 |
| 2016/0095598 A1* | 4/2016 | Khan .................. A61B 17/064 606/143 |

* cited by examiner

*Primary Examiner* — Tuan V Nguyen
(74) *Attorney, Agent, or Firm* — Donald K. Jones

(57) ABSTRACT

A system includes a first tube, a sharp coil at a distal end of the first tube, a second tube displaceable within the first tube, and a sharp housing at a distal of the second tube for storing fasteners. The housing can be positioned at a first tissue, and the coil rotated to advance the coil into engagement with the first tissue. The first tube is retracted to retract the first tissue, and then a first fastener is deployed at the first tissue location. Then, without removing the system from the patient, the distal end of the system is moved adjacent a second tissue location, and the process is repeated for a second fastener at the second tissue location. A suture extends between the first and second fasteners, and tension is applied to the suture to draw the first and second tissues toward each other to reconfigure the tissue.

45 Claims, 9 Drawing Sheets

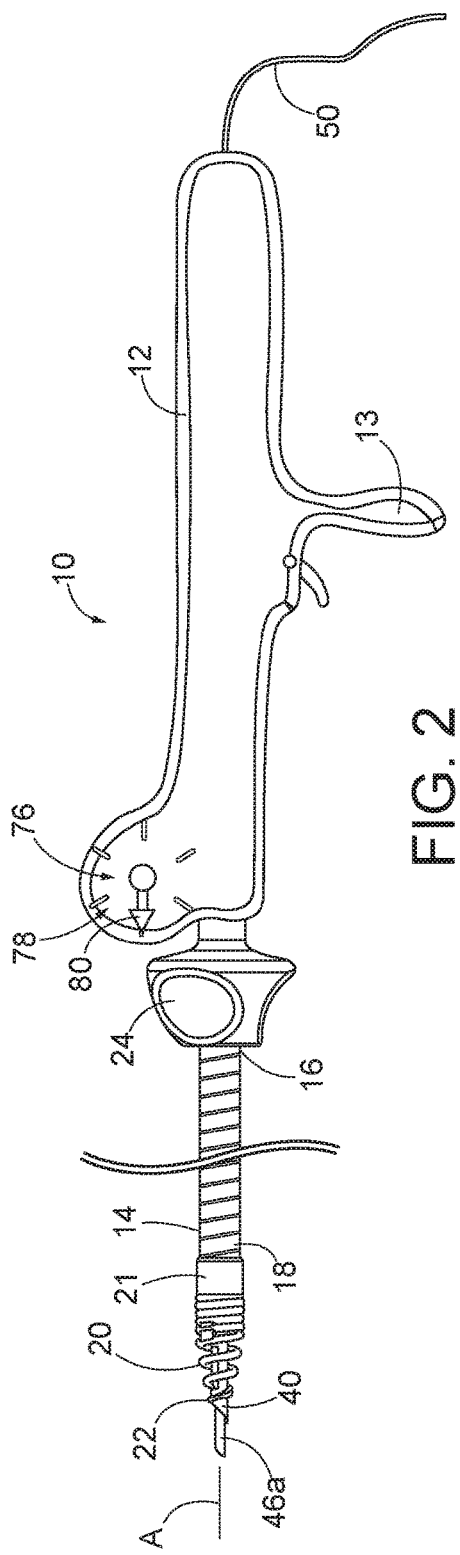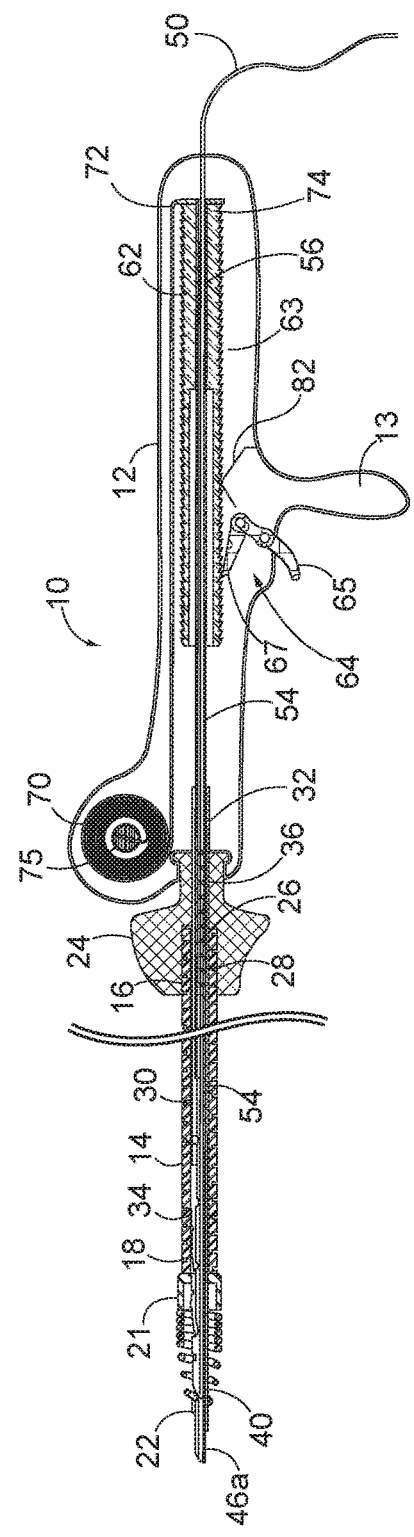

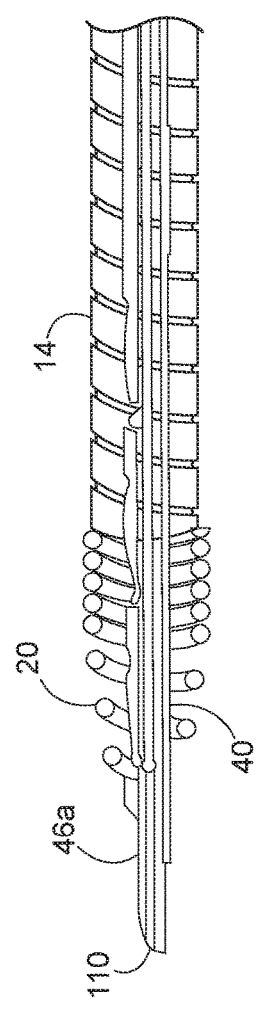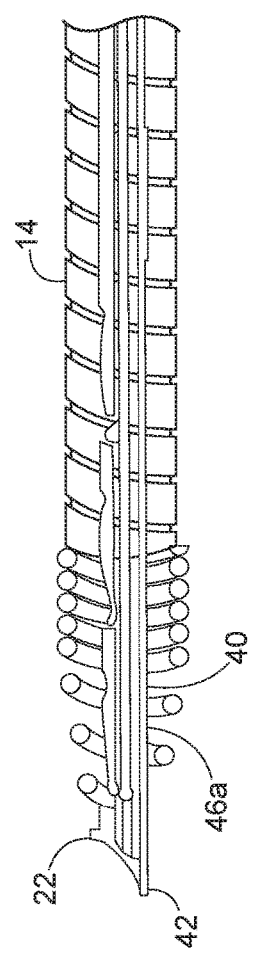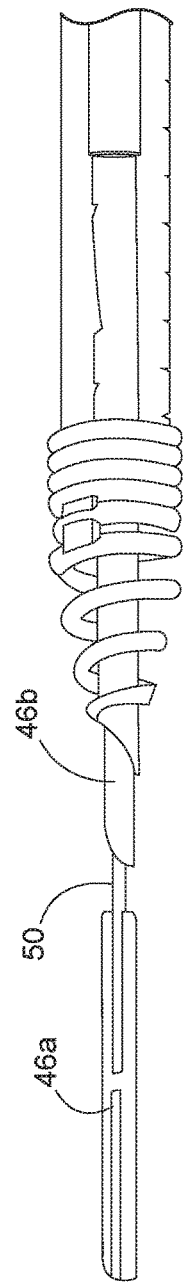

SURGICAL FASTENER DEPLOYMENT SYSTEM

BACKGROUND

Field of the Invention

The present disclosure relates to surgical instruments and methods. More particularly, the disclosure relates to instruments for deploying fasteners, as well as suturing methods and devices for use in endoscopic, laparoscopic, and other surgically open or minimally-invasive procedures.

State of the Art

The condition of obesity means an individual has too much body fat and also that an individual's weight is higher than what is considered to be healthy for their height. Biology plays a big role in why some people become obese, but not getting enough exercise, eating more food than the body can use, and drinking too much alcohol also contributes to people becoming obese. Obesity is a major health threat because excess weight puts more stress on every part of the body and puts people at risk of several health problems, such as diabetes, heart disease, and stroke.

The recommended methods for weight loss are dietary restriction and behavioral modification, including exercise. However, many persons are unable to achieve significant or sustained results using these methods. Medications for losing weight are available on the market, but some can have serious side effects and may not actually be effective for all individuals requiring weight loss. For obese individuals who cannot lower their amount of body fat through lifestyle changes or medications, various surgical options have become available.

One procedure involves surgically reducing the size of the individual's stomach by creation of a gastric pouch. While this procedure has proven successful in many cases, it has significant morbidity. Attempts to reduce morbidity by performing this procedure endoscopically have been hampered by certain limitations in endoscopic suturing techniques. Some of these limitations include the ability to accurately and selectively target the intended tissue for reconfiguring or approximating while excluding non-targeted tissues and organs.

These limitations in endoscopic suturing techniques also hamper other endoscopic procedures involving the stomach and other organs that include creating anastomoses, closing perforations in the GI tract and tissue reconfiguring procedures for treating ulcers. For example, a number of open surgical procedures have been developed for controlling gastroesophageal reflux disease. Illustratively, in one such procedure, rings are created about the proximal stomach that act as a barrier to the unraveling of the lower esophageal sphincter. However, when these procedures are carried out endoscopically, limitations in endoscopic suturing techniques make the procedures difficult.

One solution has been proposed in US2007/0276408 to Filipi et al., wherein an instrument is described that is removably or permanently attached to the end of an endoscope or integrally fabricated with the endoscope. The described instrument includes a belt with a number of slots that carry a plurality of T-fasteners in a side-by-side circumferential arrangement. The T-fasteners are connected to each other by a continuous suture. The belt can be rotated about the end of the endoscope so that the slots, and consequently the T-fasteners, are moved into alignment with a push rod positioned within a working channel of the endoscope. Operation of the push rod can advance an aligned T-fastener out of the belt and into tissue, while the deployed T-fastener remains coupled to the suture. After each deployment of a T-fastener, the belt is rotated to displace an adjacent T-fastener into alignment with the push rod, and the push rod is again operated to deploy a subsequent T-fastener. The process is repeated to deploy additional T-fasteners. After the T-fasteners are deployed into the tissue, the suture can be tensioned to draw the fastened tissue into apposition and then cinched relative to the tissue to maintain the tension to permanently reduce the space between the fasteners. Thus, in one procedure, the volume of the stomach can be reduced to treat obesity or, in another procedure, the lower esophageal sphincter can be reinforced to reduce gastroesophageal reflux.

However, the Filipi et al. system has several disadvantages that render its use impractical. First, in various embodiments, the system may require modification of a standard endoscope, either by permanent attachment thereto or integral fabrication of the system at the distal end thereof. However, surgeons are known to prefer to use the endoscopes with which they are familiar, and would not readily permanently modify a very costly endoscope for a limited use purpose. Second, the system in all embodiments has a diameter larger than the end face of the standard endoscope. This results in a bulky instrument that is less maneuverable and somewhat unwieldy when operating in tight spaces or small body cavities. Third, the system requires that the belt and all fasteners on board be driven in a rotational movement at the distal end of the endoscope so that the belt and each subsequent T-fastener can be advanced into alignment with the push rod for T-fastener deployment. Such mechanical movement is difficult to effect at the distal end of the endoscope. Any misalignment would result in a failure to deploy a T-fastener or misfire of T-fastener. Fourth, the T-fasteners are deployed without knowledge of what tissue lies behind the target tissue. Therefore, it is possible for a deployed T-fastener to pierce unintended tissue behind the target tissue and cause damage. Fifth, it appears that the system, in practicality, requires deployment of all T-fasteners loaded into the slots of the belt before the endoscope may be withdrawn from over suture for securing the suture with a cinch. Therefore, the system is not particularly suited to flexible surgical procedure. For these and other reasons, a need remains for new devices and methods.

SUMMARY

A fastener, an arrangement of a plurality of fasteners, a deployment system for deploying one or more fasteners along with suture into tissue, and methods are provided herein.

The fastener is of a type commonly referred to as a T-fastener or a T-tag. The fastener is a unitary element, consisting of a portion of substantially rigid tube that is adapted to extend over suture. The tube is preferably a portion of a hypotube. The tube includes a peripheral side wall, a longitudinal axial bore sized to receive the suture, and a longitudinal slot from the bore through the entire length of the side wall, with the exception of a suture retainer at a longitudinally central location of the tube. In one embodiment, the suture retainer is a cross bar bridging longitudinal slot. The tube preferably has blunt distal and proximal ends. The ends are preferably oriented non-orthogonal relative to the axial bore, with the distal end preferably obliquely angled toward the longitudinal slot, and the proximal end preferably obliquely angled away from the longitudinal slot and in a manner that would allow the distal end of a proximally-adjacent fastener to mate against it with end-against-end surface contact.

A plurality of like fasteners may be arranged in such end-against-end contact, with a suture extending through the axial bores of each. The distal end of the suture is provided with an end structure that restricts its movement against the suture retainer of a distalmost first fastener. Such end structure may include an enlarged knot or an attached bead that function as a stop against the suture retainer; alternatively, the end structure may be directly attached to the suture retainer via tying thereto. In such alternative, the suture retainer of the first fastener may be bent into the axial bore so that the tied suture remains below the outer surface of the side wall of the tube. The other fasteners may be longitudinally displaced along the suture at their axial bores without any significant resistance between the fastener and the suture. The suture can be drawn at a perpendicular angle relative to each fastener at its suture retainer.

A fastener deployment system is provided for deploying a plurality of the fasteners in sequence in a surgical procedure. The deployment system is preferably adapted for endoscopic or laparoscopic use, but may also be used in open surgical procedures.

The deployment system includes a proximal stationary handle, an outer tubular member having proximal and distal ends, the proximal end of the outer tubular member rotatably coupled to the handle, and a tissue-engaging coil at the distal end of the outer tubular member. A knob is provided at the proximal end of the outer tubular member to rotate the outer tubular member relative to the stationary handle. The system also includes an inner tubular member having proximal and distal ends, the proximal end rotatably coupled relative to the stationary handle. A fastener housing is coupled to the distal of the inner tubular member. The tissue-engaging coil is preferably rotationally fixed relative to the fastener housing. The fastener housing includes a sharpened, tissue piercing end, a plurality of fastener bays, each for receiving a respective fastener, and a leaf spring at each fastener bay to retain the fasteners in their bays until a sufficient force is applied to advance the fasteners forward by one bay, and the first fastener out of the fastener housing. In an embodiment, the fastener housing is adapted to retain three axially arranged fasteners, with suture as described above. A hollow push rod having proximal and distal ends extends through the handle, the inner tubular member, and into the fastener housing. The distal end of the push rod is structured to abut the proximalmost fastener. The proximal end of the push rod extends to a rack. A lever is mounted to the handle and adapted to engage the rack such that when the lever is actuated, the rack and the push rod are distally advanced to apply a longitudinal force against the linear arrangement of fasteners and deploy the first fastener. A constant force spring is provided in the handle and has a first end in contact with the rack, and a second end coupled to an indicator. The constant force spring compensates for discrepancy between the lengths of the push member and the inner tubular member when the system is navigated through a tortuous path. The indicator provides visual and/or auditory feedback that the fastener is ready to be safely deployed into tissue and of the number of fasteners deployed from or remaining within the system. By way of example, the indicator may include a gauge and dial and/or lights for visual feedback. The indicator may alternatively or additionally include a mechanical clicker or auditory transducer to generate a feedback sound.

In an embodiment, the outer tubular member and tissue-engaging coil are sized to extend within the working channel of an endoscope. In the same embodiment, the outer tubular member, inner tubular member and push rod are all sufficiently flexible for use within the working channel of an endoscope that extends through a tortuous path, and particularly through the working channel of an endoscope that is retroflexed.

Fasteners are provided within each of the bays of the needle housing, with a suture retained relative to the distalmost first fastener and extending through a proximal portion of the first fastener and the entire axial bores of the remaining fasteners, through the hollow push rod and rack, proximally beyond the first end of the constant force spring, and out of the handle. The distal end of the first fastener protrudes beyond both the fastener housing and tissue-engaging coil.

In use, the outer tubular member is advanced through or pre-positioned within a working channel of an endoscope or lumen. In one method, the endoscope is positioned within a natural body orifice, such as the gastroesophageal tract, and has its distal end located within the stomach. The distal end of the deployment system is advanced out of the working channel, and the blunt protruding distal end of the distalmost fastener is forced against a first target tissue location in which the first fastener is to be deployed. As the fastener contacts the first target tissue location, the first fastener retracts into the fastener housing against the force of the constant force spring and flush with the sharp tip of the fastener housing. The dial indicates the force against the constant-force spring to show and thereby indicates that the first fastener is in contact with tissue and under retraction. The sharp tip of the fastener housing penetrates the tissue up until the distal end of the tissue-engaging coil. Then, the knob at the proximal end of the outer tubular member is rotated relative to the stationary handle to rotatably advance the tissue-engaging coil into the tissue to engage the tissue. The stationary handle is next retracted relative to the tissue to draw the engaged tissue away from any underlying tissue (to prevent penetration of unintended tissue), and the tissue-engaging coil is further rotated to advance the sharp tip of the fastener housing through the tissue. Once through the tissue, the counter force against the distalmost fastener will be removed, and the dial indicates the reduced force. The lever is then actuated with sufficient force to advance the rack and the push rod and move the arrangement of fasteners against the constraint of their respective leaf springs into a relatively distal bay and the distalmost fastener to be deployed out of the fastener housing and completely through the first target tissue location. Actuation of the lever with the force to deploy a fastener decrements (or increments) a count on the dial corresponding to the number of fasteners remaining for use (or used) during the procedure. The knob is then counter-rotated to release the tissue-engaging coil from the tissue. Once on the opposing side of the first target tissue location, the first fastener will rotate into contact with the tissue and the suture will extend from the first fastener through the first target tissue location back through the axial bores of the remaining fasteners and the deployment system.

The distal end of the deployment system is then moved to a second target tissue location, and the process is repeated to engage tissue, retract tissue, deploy a subsequent fastener, and release the tissue. The process is repeated as necessary to locate fasteners at various locations suitable for a therapeutic treatment.

Once the fasteners have been deployed into the tissue, the deployment system can be withdrawn from the working channel and over the suture. A cinch device is then advanced over the suture, preferably through the same working channel. The suture is tensioned to drawn the suture through the fasteners and consequently the first, second, etc. target tissue locations into apposition. Once the appropriate tension is applied to achieve tissue reconfiguration, the cinch is secured to the suture retain the tissue reconfiguration. Alternatively, no cinch is required and the suture may be tied to retain the tension thereon.

The fastener deployment system provides several advantages. It can be deployed through a working channel of a conventional endoscope, and requires no modification to the endoscope. The deployment system does not increase the overall diameter of the distal end of the endoscope. The deployment system is adapted to penetrate tissue with a fastener safely. It has a mechanism to prevent penetration of adjacent tissue, including an indicator that indicates when it is safe to deploy a fastener.

BRIEF DESCRIPTION OF THE DRAWINGS

FIG. 2 is a broken side elevation view of the fastener deployment system.

FIG. 3 is a broken longitudinal section view of the fastener deployment system.

FIGS. 10A through 18 illustrate a use of the fastener deployment system, with

FIG. 10A showing the distal end of the fastener deployment system advanced through an endoscope, FIG. 10B showing an enlarged view of the distal end of the fastener deployment system of FIG. 10A, and FIG. 10C illustrating the proximal handle configuration corresponding with FIGS. 10A and 10B, FIG. 11A showing the distal end of the fastener deployment system advanced partially into a first tissue location, FIG. 11B showing an enlarged view of the distal end of the fastener deployment system of FIG. 11A, and FIG. 11C illustrating the proximal handle configuration corresponding to FIGS. 11A and 11B, FIG. 12A showing the distal end of the fastener deployment system advanced completely through the first tissue location and with the tissue retracted, and FIG. 12B illustrating the proximal handle configuration corresponding to FIG. 12A, FIG. 13A showing a first fastener deployed through the first tissue location, FIG. 13B showing an enlarged view of the distal end of the fastener deployment system of FIG. 13A, and FIG. 13C illustrating the proximal handle configuration corresponding to FIGS. 13A and 13B, FIG. 14 showing the proximal handle configuration reset for a deployment of a subsequent fastener, FIG. 15 showing rotation of a fastener positioned within a first tissue location, FIG. 16 showing deployment of a second fastener at a second tissue location, FIG. 17 showing deployment of a third fastener at a third tissue location, and FIG. 18 showing reconfiguration of the first, second and third tissue locations relative to each other, and cinching of the suture.

DETAILED DESCRIPTION OF PREFERRED EMBODIMENTS

With reference to the following description, the terms "proximal" and "distal" are defined in reference to the hand of a user of the device, with the term "proximal" being closer to the user's hand, and the term "distal" being further from the user's hand such as to often be located further within a body of the patient during use. Further, in accord with a general description of the system and its exemplar use, described in more detail below, the system is provided and used to target tissue, deploy a fastener into tissue, and reconfigure the fastened tissue. Such targeting, fastening and reconfiguring are preferably, though not necessarily, performed in conjunction with a surgical scope, such as a laparoscope or an endoscope. In embodiments described herein, the steps may be used to reconfigure tissue through or with the aid of an endoscope in which the instrument acting to reconfigure the tissue are inserted through a natural orifice, namely the gastroesophageal pathway, preferably without incision to either the dermal or internal tissues of a patient in order to effect for passage of the required instruments. Specifically, it is recognized that piercing the tissue for insertion of a fastener does not effect an incision in the tissue.

Figure 1:
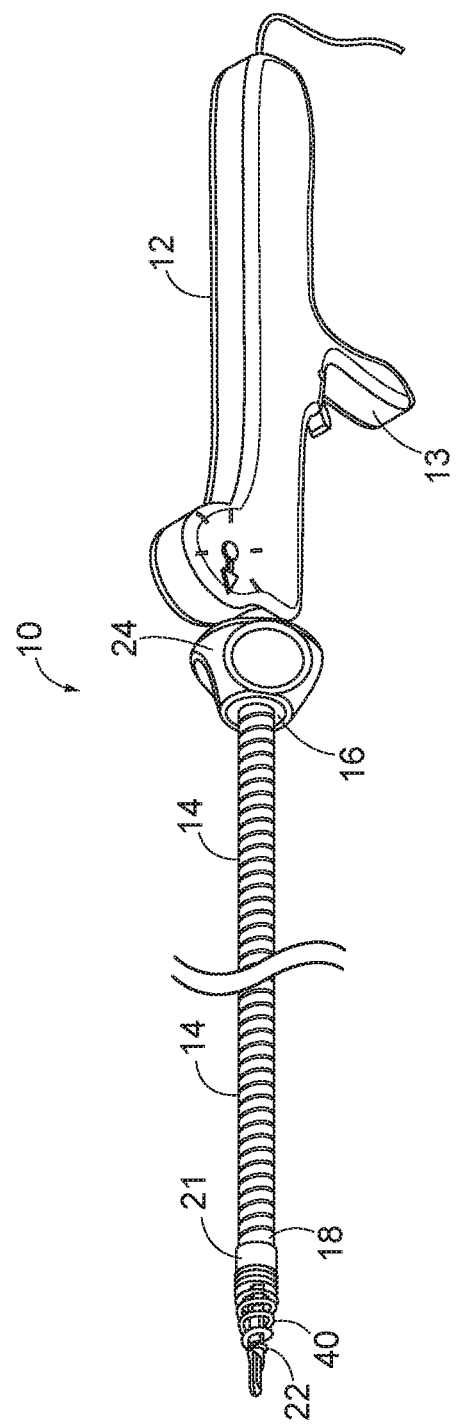
FIG. 1 is a broken perspective view of a fastener deployment system.

Turning now to FIGS. 1 through 3, a fastener deployment system 10 is shown. The system 10 includes a stationary proximal handle 12 including a hand grip 13, an outer, first tubular member 14 having a proximal end 16 and a distal end 18 and defining a longitudinal axis A, and a distal, tissue-engaging coil 20 rotationally fixed to the distal end 18 of the first tubular member via collar 21. The first tubular member 14 is preferably constructed as a flexible, tightly wound, flat metal coil. The distal coil 20 is preferably tapered, and has a tissue-piercing distal tip 22. The distal coil 20, including its tip 22, does not have any exposed sharps in the longitudinal direction, and is only adapted to pierce tissue upon rotation. A knob 24 is rotatably coupled to the handle 12. The knob includes a stepped throughbore 26, with the proximal end 16 of the first tubular member 14 fixed within a larger distal portion 28 of the throughbore 26 such that rotation of the knob relative to the handle result in rotation of the first tubular member 14 and the coil 20. An inner, second tubular member 30 has a proximal end 32 and a distal end 34 and extends through the first tubular member 14. The second tubular member 30 is preferably a flexible polymeric catheter. The proximal end 32 is fixed within a smaller proximal portion 36 of the throughbore 26. The distal end 34 is provided with a fastener housing 40. The fastener housing 40 extends within, and is preferably rotationally fixed relative to, the tissue engaging coil 20, e.g., the collar 21. Brazing, welding, bonding or adhesives, or other suitable means may be used to join the coil 20 and housing 40 to the collar 21. The minimum diameter of the tissue-engaging coil 20 preferably corresponds to the outer diameter of the fastener housing 40 such that the two are close fitting.

Figure 4:
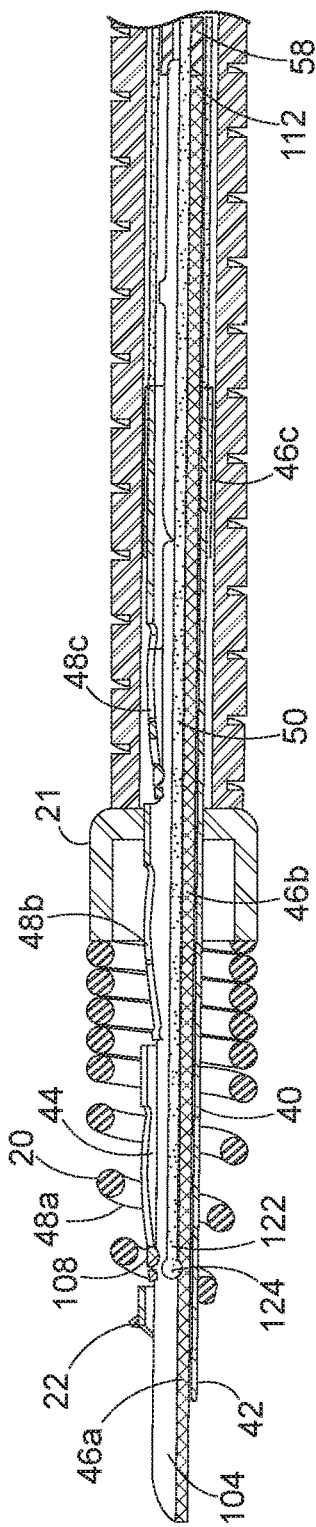
FIG. 4 is an enlarged longitudinal section view of the fastener deployment system.
Figure 5:
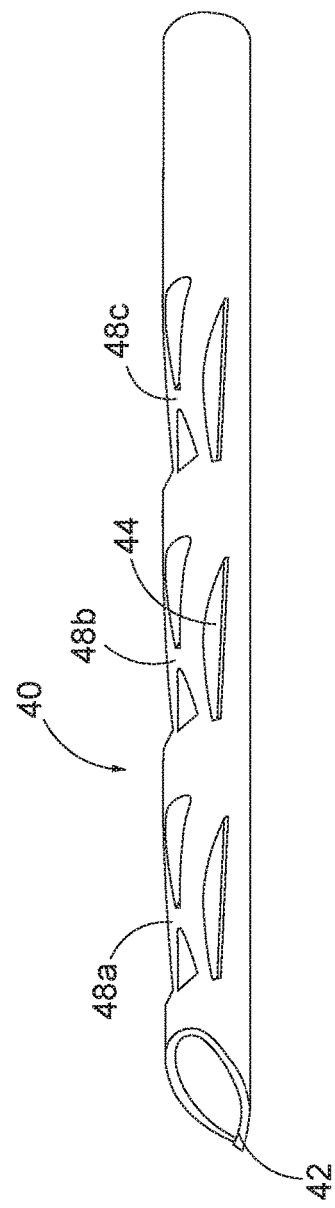
FIG. 5 is a perspective view of a fastener housing of the fastener deployment system.

Referring to FIGS. 4 and 5, the fastener housing 40 includes a sharpened, tissue piercing end 42, a fastener bay 44 for receiving the fasteners 46a, 46b, 46c (collectively 46), and leaf springs 48a, 48b, 48c that extend into the bay to retain the fasteners in the bay 44 until a sufficient force is applied to longitudinally advance the fasteners forward past a leaf spring 48a, 48b, 48c and, consequently, the distalmost, first fastener 46a out of the housing 40. The housing 40 is preferably a unitary construct formed form a portion of a hypotube. While the housing 40 is shown with a bay 44 approximately two fastener lengths for axially receiving portions of three fasteners 46, the housing and bay may be provided in different lengths to store an alternate number of fasteners. The fasteners 46 and a suture 50 extending through them are described in more detail below.

Referring to FIGS. 3 and 4, a hollow push rod 54 extends through the second tubular member 30, and has a proximal end 56 and a distal end 58. The distal end 58 extends into contact with the proximal end 112 of a proximalmost fastener 46c. The proximal end 56 of the push rod 54 extends into the handle 12 and is coupled to a toothed rack 62 that is adapted to longitudinally displace the distal end 58 of the push rod 54 relative to the housing 40. The toothed rack 62 has teeth 63 obliquely angled in a proximal direction. A lever 64 is mounted to the handle and adapted to engage the toothed rack 62 such that when the lever 64 is actuated, the toothed rack 62 and the push rod 54 are distally advanced to longitudinally displace the distal end 58 of the push rod 54 and apply a longitudinal force against the linear arrangement of fasteners 46 and deploy the first fastener 46a. The lever 64 is preferably comprised of a trigger 65 and a trigger pin 67 coupled at an end of the trigger with a torsion or leaf spring (not shown) that forces the trigger pin into engagement with the teeth 63 of the rack 62. The angle of the teeth 63 results in engagement between the trigger pin 67 and the teeth 63 when the lever is actuated. The angle of the teeth 63 also allows the trigger pin 67 to be relatively freely moved proximally along the teeth to automatically cock the trigger 65. A spring (not shown) may be provided to cock the trigger 65 after the lever 64 is actuated. As an alternative to the lever 64, a button, rotatable knob, a crank or other actuator may be utilized to actuate longitudinal displacement of the push rod 54 relative to the housing 40.

Referring to FIGS. 2 and 3, a constant force spring 70 is provided in the handle 12 and has a first end 72 in contact with a proximal end 74 of the rack 62, and a second end 75 coupled to an indicator 76. When the lever 64 is not being actuated, the constant force spring 70 compensates for any discrepancy between the lengths of the inner tubular member 30 and the push rod 54 that could otherwise occur when the system 10 is navigated through a tortuous path. The indicator 76 provides feedback that the distalmost fastener 46a is ready to be safely deployed into tissue, that the fastener has been deployed, and of the number of fasteners deployed from or remaining within the system. By way of example, the indicator 76 may include a dial 78 and a gauge 80 that displaces relative to the dial to indicate a force countering the resistance of the constant force spring 70. In addition or as an alternative to a dial and gauge, the system may include other visual feedback indication, including one or more lights. For example, a light may indicate red when it is, under the standards of the system, unsafe to deploy a fastener, and green when it is, under the standards of the system, safe to deploy a fastener. As another example, a numeric mechanical or electric display indicator may indicate the number of fasteners deployed from the system, the number of fasteners remaining within the system, or both. A mechanical clicker or an auditory transducer may be used to generate a feedback sound to confirm that the lever 64 has been actuated. For example, a leaf spring 82 fixed to the handle 12 and engaged relative to the rack 62 generates an audible clicking sound when the lever 64 is actuated to advance the rack 62, and thereby provides feedback that the lever has been actuated to deploy a fastener.

In an embodiment, the fastener deployment system 10 is sized to extend within the working channel of an endoscope from the proximal handle of the endoscope to beyond the distal end face of the endoscope; for example a first tubular member 14 length of 60-100 cm and a first tubular member outer diameter of 2-6 mm. In the same embodiment, the first tubular member 14, second tubular member 30, and push rod 54 are all sufficiently flexible for use within the working channel of an endoscope that extends through a tortuous path, and particularly through the working channel of an endoscope that is retroflexed.

Figure 6:
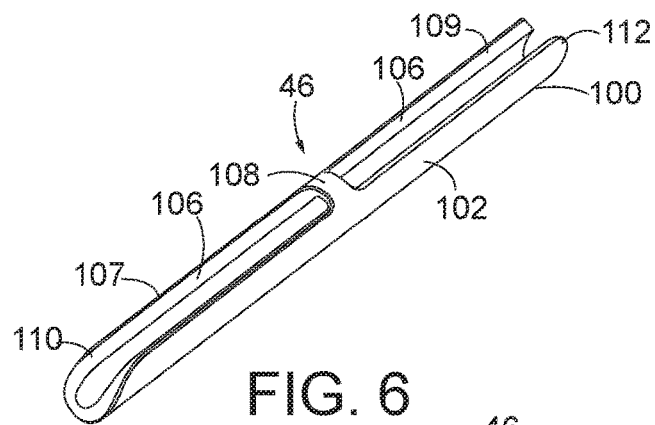
FIG. 6 is a perspective view of an embodiment of a fastener for use in the fastener deployment system.
Figure 7:
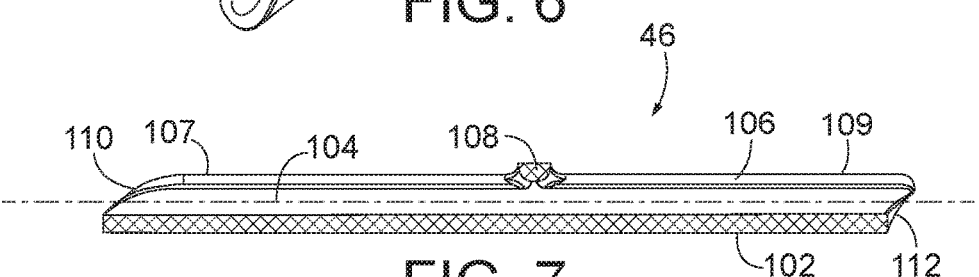
FIG. 7 is a longitudinal section view of the fastener in FIG. 6.

Turning now to FIGS. 6 and 7, the fastener 46 is shown in more detail. The fastener is of a type commonly referred to as a T-fastener or a T-tag. The fastener 46 is a unitary element, consisting of a portion of substantially rigid tube 100, such as a hypotube. The tube 100 includes a peripheral side wall 102, a longitudinal axial bore 104 sized to receive a suture therethrough, and a longitudinal slot 106 extending from the bore 104 through the entire length of the side wall 102, with the exception of a suture retainer 108 at a longitudinally central location of the tube. In one embodiment, the suture retainer 108 is a cross bar bridging longitudinal slot. The tube 100 has a distal portion 107 with a distal end 110, and a proximal portion 109 with a proximal end 112. The ends 110, 112 are blunt and preferably oriented non-orthogonal relative to the axial bore 104, with the distal end 110 preferably obliquely angled toward the longitudinal slot 106, and the proximal end 112 preferably obliquely angled away from the longitudinal slot 106. The distal and proximal ends of the fastener are configured such that like fasteners can be provided in an end-to-end arrangement of high surface area contact. The proximal end 112 of a distally-adjacent fastener is preferably configured and adapted to overhang a distal end 110 of a proximally-adjacent like fastener.

Referring to FIGS. 4, 6 and 7, a plurality of like fasteners may be arranged in such end-against-end contact, with the suture 50 extending through the axial bores 104 of each fastener. The distal end 122 of the suture 50 is provided with an end structure 124 that restricts its movement against the suture retainer 108 of the distalmost first fastener 46a. Such end structure 124 may include an enlarged knot 126 or an attached bead that function as a stop against the suture retainer; alternatively, the distal end 122 may be directly attached to the suture retainer via tying thereto. In such alternative, the suture retainer 108 of the first fastener 46a may be bent into the axial bore 104 so that the tied suture remains below the outer surface of the side wall 102 of the tube. The other fasteners 46b, 46c are longitudinally displaced along the suture 50 without any significant resistance between the fasteners and the suture. The suture 50 can be drawn at a perpendicular angle relative to each fastener at its suture retainer.

Figure 8:
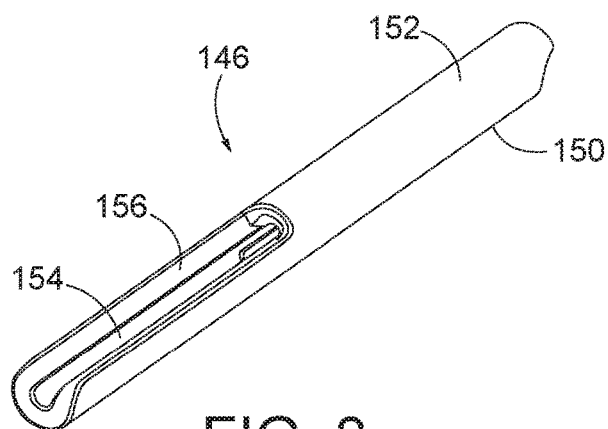
FIG. 8 is a perspective view of another embodiment of a fastener for use in the fastener deployment system.
Figure 9:
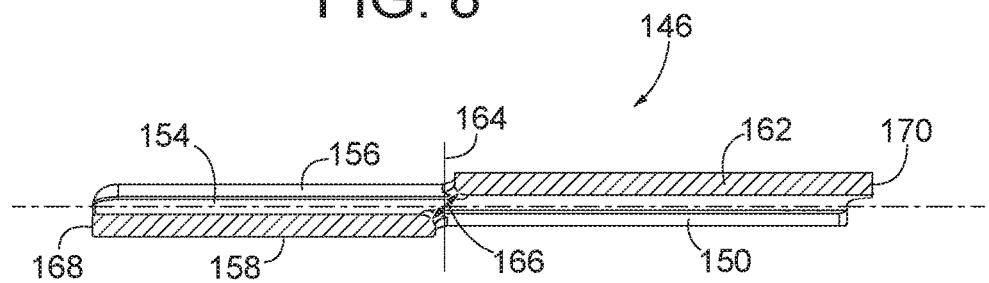
FIG. 9 is a longitudinal section view of the fastener in FIG. 8.

Referring to FIGS. 8 and 9, an embodiment of an alternate T-tag fastener 146 for use in the deployment system is shown. Fastener 146 is a unitary element, consisting of a portion of substantially rigid tube 150, such as a hypotube. The tube 150 includes a peripheral side wall 152, a longitudinal axial bore 154 sized to receive a suture therethrough, and a first slot 156 extending from the bore 104 through a distal, first portion 158 of the tube (approximately one half the length of the side wall 102), and an opposite second slot 160 along a proximal, second portion 162 of the tube (approximately the other half of the length of the side wall 152). The first and second slots 156, 160 overlap such that a transverse passageway 164 is provided through the fastener of a size sufficient to pass a suture. When the fastener 146 is loaded over the suture, with the suture extending within its axial bore 154, the fastener can be rotated 90° on the suture, from the axial bore 154, through the slots 156, 160 and into the passageway 164. The limited size of the opening 166 at the passageway 164 functions as a suture retainer for a distal end of the suture. The distal and proximal ends 168, 170 of the fastener are configured such that like fasteners can be provided in an end-to-end arrangement of high surface area contact. In a preferred embodiment, the proximal end 170 is adapted to overhang the distal end 168 of a proximally adjacent fastener of like configuration. Other suitable fastener configurations may also be used.

Referring back to FIGS. 3, 4, and 6, fasteners 46 are provided within the bay 44 of the housing 40, with the suture 50 retained relative to the distalmost first fastener 46a and extending through the proximal portion 109 of the first fastener 46a and the entire axial bores 104 of the remaining fasteners 46b, 46c, through the hollow push rod 54 and rack 62, proximally beyond the first end 72 of the constant force spring 70, and out of the handle 12. The distal end 110 of the first fastener 46a protrudes beyond both the fastener housing 40 and tissue-engaging coil 20.

Now, in accord with a method of using the deployment system 10, an endoscope is advanced through a natural body orifice, such as the gastroesophageal tract, so that its distal end is located within a body cavity such as the stomach. The distal portion of the deployment system 10 is advanced through or pre-positioned within the working channel of the endoscope. Alternatively, the deployment system may be advanced through a peripheral lumen external of the endoscope.

Figure 10A:
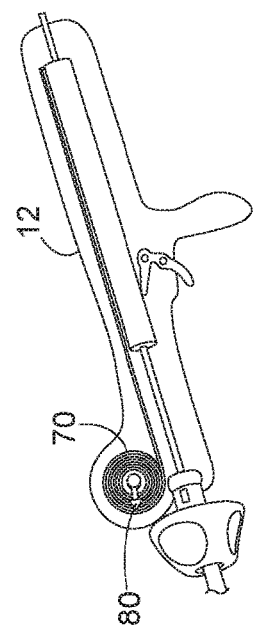
Figure 10C:
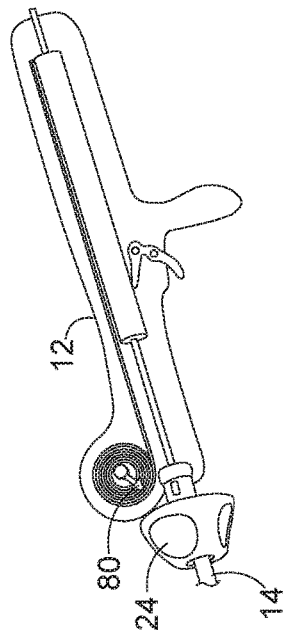

Referring to FIGS. 10A, 10B and 10C, the distal end of the deployment system, e.g., the protruding distal end of the first fastener 46a, the housing 40, and the tissue-engaging coil 20, is advanced out of the working channel 204 of the endoscope 200 (or other lumen). The blunt protruding distal end 110 of the first fastener 46a is not yet in contact with a first target tissue location 206. The gauge 80 on the handle 12 indicates no counterforce against the spring 70 at the distal end of the system.

Figure 11A:
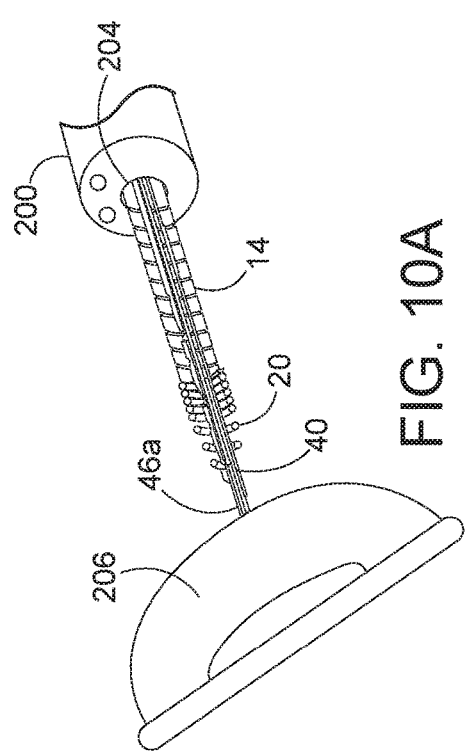
Figure 11C:
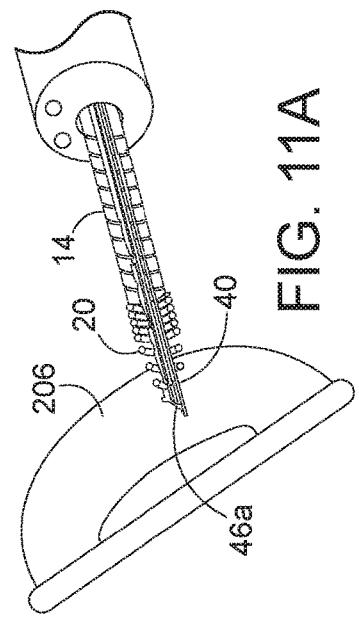

Turning now to FIGS. 11A, 11B and 11C, as the distal end 110 of the first fastener 46a is positioned at and forced against the first target tissue location 206, the first fastener is pushed by the tissue counter to the force of the constant force spring 70, and retracted into the housing 40 substantially flush with the sharp tip 42 of the housing 40. The gauge 80 indicates the force against the constant-force spring 70 and thereby indicates, at the proximal end of the system and to the user, that the first fastener 46a is in contact with the tissue 206 and under retraction. The sharp tip 42 of the fastener housing 40 penetrates the first tissue location 206 up until the distal end 22 of the tissue-engaging coil 20. Then, the knob 24 coupled at the proximal end of the outer tubular member 14 is rotated relative to the stationary handle 12 to rotatably advance the tissue-engaging coil 20 into the tissue to engage the tissue. Because the housing 40 rotates with the tissue-engaging coil 20, the suture 50 is prevented from tangling about the coil during coil rotation.

Figure 12A:
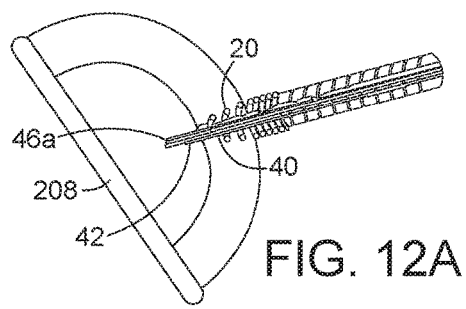
Figure 12B:
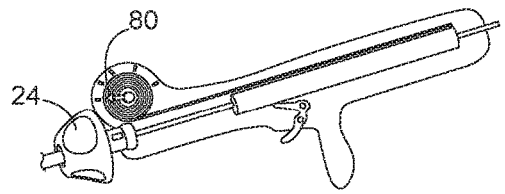

Referring now to FIGS. 12A and 12B, the stationary handle 12 is next retracted relative to the engaged tissue 206 to draw the engaged tissue away from any underlying tissue 208 (to prevent penetration of unintended underlying tissue), and the tissue-engaging coil 20 is further rotated to advance the sharp tip 42 of the housing 40 through the tissue. Once through the tissue 206, the counter force against the distalmost fastener 46a will be removed, and the gauge 80 indicates the reduced force.

Figure 13A:
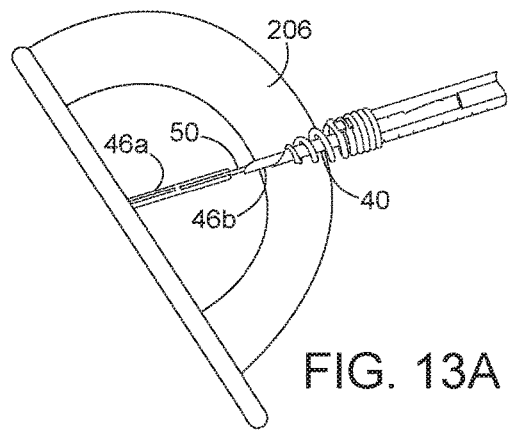
Figure 13C:
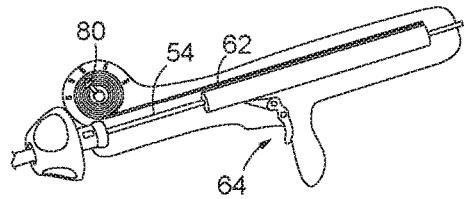

Turning to FIGS. 13A and 13B, the lever 64 is then actuated with sufficient force to advance the rack 62 and the push rod 54 and move the arrangement of fasteners 46 against the constraint of their respective leaf springs 48 into a relatively distally within the bay and the distalmost fastener 46a to be deployed out of the fastener housing 40 and completely through the first target tissue location 206. The subsequent fastener 46b now protrudes through the fastener housing 40 and the suture 50 extends between the fasteners. Actuation of the lever 64 with the force to deploy a fastener decrements (or increments) a count on the gauge 80 corresponding to the number of fasteners remaining for use (or used) during the procedure.

Figure 14:
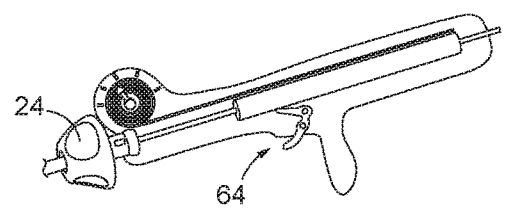

Referring to FIG. 14, the knob 64 is then counter-rotated to release the tissue-engaging coil from the tissue. The lever 64 is reset for subsequent actuation.

Figure 15:
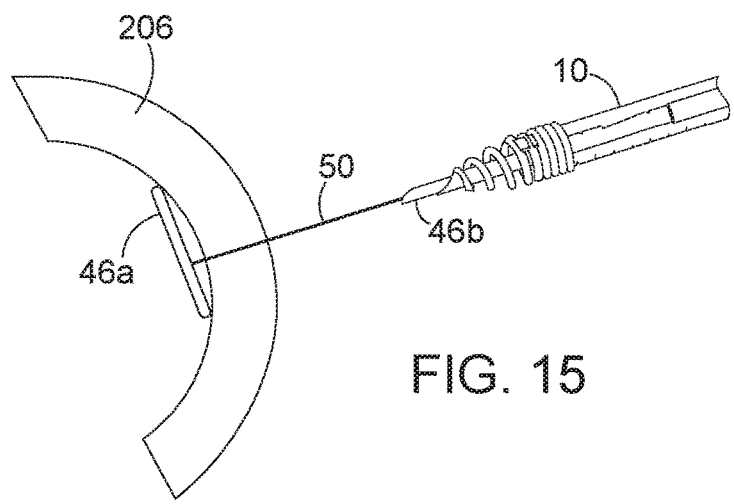

Once on the opposing side of the first target tissue location, the first fastener 46a will rotate into contact with the tissue and the suture 50 will extend from the first fastener 46a through the first target tissue location 206 back through the axial bores of the remaining fasteners 46b, (46c) and the deployment system 10 (FIG. 15).

Figure 16:
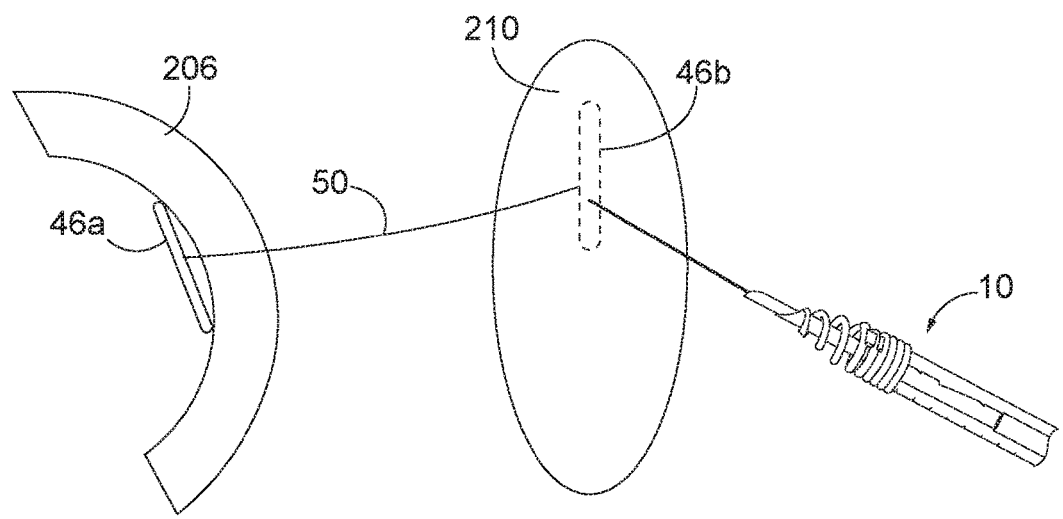
Figure 17:
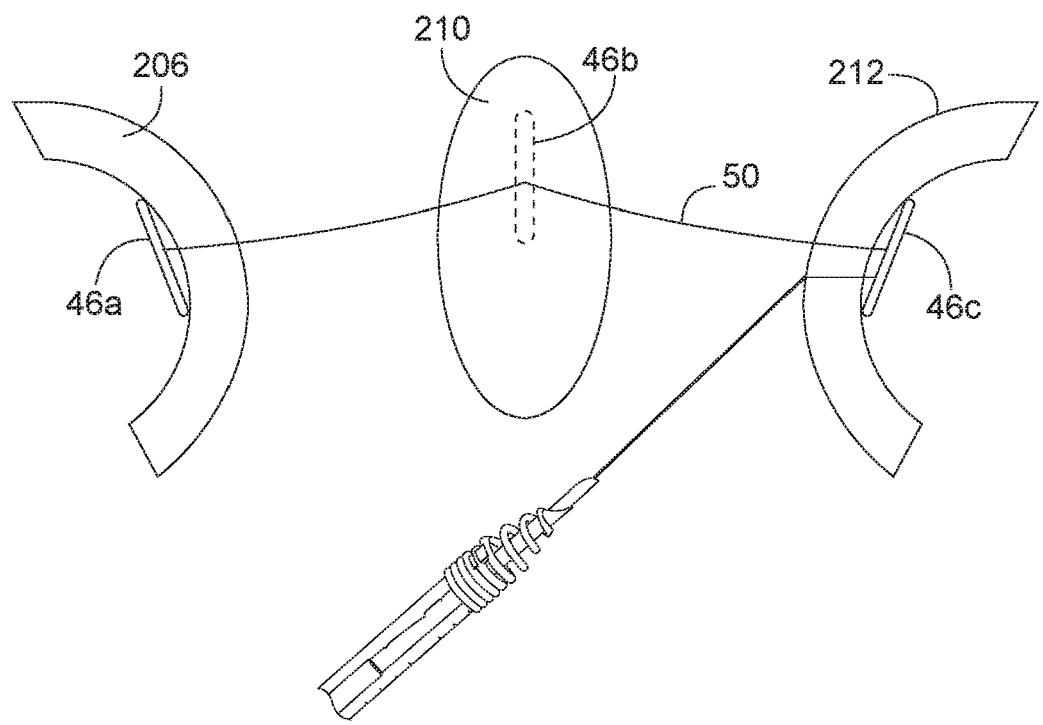

The distal end of the deployment system 10 is then moved to a second target tissue location 210, and the process is repeated to engage tissue, retract tissue, deploy a subsequent fastener 46b, and release the tissue relative to the deployment system (FIG. 16). The process may be repeated with a third fastener 46c at a third tissue location 212 (and as necessary) to locate fasteners at various locations suitable for a therapeutic treatment (FIG. 17).

Figure 18:
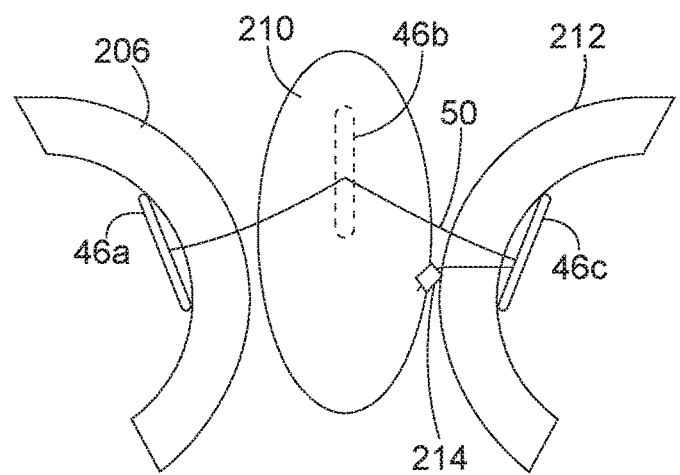

Once the fasteners 46a, 46b, 46c have been deployed into their respective locations 206, 210, 212, the deployment system can be withdrawn from the working channel and over the suture 50. A cinch device (not shown) is then advanced over the suture 50, preferably through the same working channel. Referring to FIG. 18, the suture 50 is tensioned to drawn the suture through the fasteners 46a, 46b, 46c and consequently the first, second, etc. target tissue locations 206, 210, 212 into apposition. Once the appropriate tension is applied to achieve tissue reconfiguration, the cinch 214 is secured to the suture 50 to retain the tissue reconfiguration. Alternatively, no cinch is required and the suture may be tied to retain the tension thereon.

There have been described and illustrated herein embodiments of a fastener deployment system for deploying one or more fasteners relative to pierced and engaged tissue, embodiments of fasteners, and methods of deploying a fastener, fastening tissue, and reconfiguring tissue. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A tissue fastener deployment system, comprising:
 a) a handle;
 b) a first tubular member having a proximal end and a distal end and defining a longitudinal axis, the proximal end rotatably coupled to the handle;

c) a coil having a tissue-piercing distal tip, the coil rotationally fixed relative to the first tubular member, such that rotation of the first tubular member relative to the handle results in rotation of the coil, wherein when the distal tip of the coil is rotated against tissue the distal tip of the coil is adapted to pierce and engage the tissue;

d) at least one fastener axially displaceable relative to the distal end of the first tubular member and through the coil;

e) a push member longitudinally displaceable relative to the first tubular member and adapted to apply an axial displacement force against the at least one fastener; and f) an actuator movably coupled relative to the handle, wherein actuating the actuator results in longitudinal displacement of the push member relative to the first tubular member and to apply an axial displacement force against the at least one fastener to deploy one of the at least one fastener from the deployment system.

2. The tissue fastener deployment system according to claim 1, wherein:
the first tubular member and the push member are sufficiently flexible to be positioned through a tortuous path.

3. The tissue fastener deployment system according to claim 1, wherein:
the first tubular member comprises a flat-wound coil.

4. The tissue fastener deployment system according to claim 1, wherein:
the coil is a tapered helix.

5. The tissue fastener deployment system according to claim 1, wherein:
the at least one fastener comprises a plurality of fasteners.

6. The tissue fastener deployment system according to claim 1, wherein:
the at least one fastener includes proximal and distal ends, a side wall, an axial bore from the proximal end to the distal end, a longitudinal slot extending through the side wall along the length of the axial bore, and a crossbar bridging across the longitudinal slot to the side wall on opposite sides of the longitudinal slot at a location between the proximal and distal ends.

7. The tissue fastener deployment system according to claim 6, wherein:
the proximal and distal ends of the at least one fastener are blunt.

8. The tissue fastener deployment system according to claim 6, further comprising:
a suture,
wherein the at least one fastener includes a plurality of fasteners, and the suture is retained relative to the crossbar of a distalmost fastener of the plurality of fasteners, and extends completely through the axial bore of each relatively proximal fastener of the plurality of fasteners.

9. The tissue fastener deployment system according to claim 1, wherein:
the at least one fastener includes blunt proximal and distal ends.

10. The tissue fastener deployment system according to claim 1, further comprising:
a constant force spring located in the handle and applying a constant force against the proximal end of the push member.

11. The tissue fastener deployment system according to claim 10, wherein:
the first tubular member and the push member are sufficiently flexible to be positioned through a tortuous path, and
when extending within the tortuous path, the constant force spring retains the distal ends of the first tubular member and push member in a fixed longitudinal relationship until the push member is acted upon by the actuator.

12. The tissue fastener deployment system according to claim 10, further comprising:
an indicator that provides at least one of visual and audio feedback of the axial displacement force applied by the actuator.

13. The tissue fastener deployment system according to claim 1, further comprising:
a second tubular member having proximal and distal ends and extending within the first tubular member, the proximal end of the second tubular member coupled to the handle; and
a fastener housing at the distal end of the second tubular member, the at least one fastener stored within the fastener housing.

14. The tissue fastener deployment system according to claim 13, wherein:
the fastener housing has a tissue-piercing distal end, and the at least fastener is displaceable proximal of the tissue-piercing distal end.

15. The tissue fastener deployment system according to claim 14, wherein:
the distal end of the fastener housing is structured to pierce tissue when axially displaced, and the coil is structured to pierce tissue when rotationally displaced.

16. The tissue fastener deployment system according to claim 13, wherein:
the fastener housing includes at least one leaf spring that each act on a respective at least one fastener with a retention force sufficient to retain the at least one fastener from no more than a maximum distal displacement until the actuator is actuated with sufficient force to overcome the retention force.

17. The tissue fastener deployment system according to claim 13, wherein:
the coil is fixed to the distal end of the fastener housing.

18. The tissue fastener deployment system according to claim 17, wherein:
a minimum diameter of the coil corresponds to an outer diameter of the fastener housing.

19. The tissue fastener deployment system according to claim 1, further comprising:
an indicator that provides an indication of a number of fasteners remaining within or deployed from the fastener deployment system.

20. The tissue fastener deployment system according to claim 1, wherein:
the push member includes a rack at a distal end thereof, and the actuator engages the rack to axially displace the push member.

21. The tissue fastener deployment system according to claim 20, wherein:
the actuator disengages from the rack after each actuation of the actuator.

22. The tissue fastener deployment system according to claim 1, wherein:
at each actuation of the actuator, the actuator couples to the push member to cause longitudinal displacement of the push member, and after each actuation of actuator, the actuator decouples from the push member.

23. A tissue fastener deployment system, comprising:
a) a handle;
b) a flexible first tubular member having a proximal end and a distal end and defining a longitudinal axis, the proximal end rotatably coupled to the handle;
c) a flexible second tubular member having a proximal end and a distal end, and extending through the first flexible tubular member;
d) a fastener housing adapted to store a plurality of tissue fasteners and provided at the distal end of the second tubular member, the fastener housing having a tissue-piercing distal tip;
e) a coil having a tissue-piercing distal tip, the coil rotationally fixed relative to the distal end of the first tubular member, wherein rotation of the first tubular member relative to the handle results in rotation of the coil;
f) a flexible push member longitudinally displaceable within the second tubular member and adapted to be axially displaced into the fastener housing; and
g) an actuator movably coupled relative to the handle, wherein actuating the actuator results in longitudinal displacement of the push member relative to the first tubular member and into the fastener housing.

24. The tissue fastener deployment system of claim 23, wherein:
the coil is rotationally fixed relative to the fastener housing such that rotation of the first tubular member relative to the handle results in rotation of both of the coil and the fastener housing.

25. The tissue fastener deployment system of claim 23, further comprising:
a plurality of fasteners stored in the fastener housing; and
a suture extending through the second tubular member.

26. A tissue fastener deployment system, comprising:
a) a handle;
b) a flexible first tubular member having a proximal end and a distal end and defining a longitudinal axis;
c) a flexible second tubular member having a proximal end and a distal end, and extending through the first flexible tubular member;
d) a fastener housing provided at the distal end of the second tubular member having a tissue-piercing end;
e) a plurality of longitudinal tissue fasteners retained within the fastener housing, the fasteners having blunt proximal and distal ends;
f) a flexible push member longitudinally displaceable within the second tubular member and adapted to be axially displaced into the fastener housing;
g) a spring applying a force to the push member to axially displace the tissue fasteners toward the tissue-piercing end of the fastener housing, the fastener housing including one or more leaf springs that limits distal displacement of the fasteners; and
h) an actuator movably coupled relative to the handle, wherein actuating the actuator results in longitudinal displacement of the push member into the fastener housing to overcome the retention of the one or more leaf springs.

27. The tissue fastener deployment system of claim 26, wherein:
a coil having a tissue-piercing distal tip, the coil fixed to the distal end of the first tubular member, and the proximal end of the first tubular member rotatably coupled to the handle.

28. A method of deploying a fastener into tissue, comprising:
a) providing a fastener deployment system having a proximal end and distal end, the deployment system including,
  i) a handle,
  ii) a first tubular member having a proximal end and a distal end and defining a longitudinal axis, the proximal end rotatably coupled to the handle,
  iii) a coil having a tissue-piercing distal tip, the coil rotationally fixed relative to the first tubular member, such that rotation of the first tubular member relative to the handle results in rotation of the coil, wherein when the distal tip of the coil is rotated against tissue the distal tip of the coil is adapted to pierce and engage the tissue, and
  iv) a fastener axially displaceable relative to the distal end of the first tubular member and through the coil;
b) positioning the distal end of the deployment system adjacent a first tissue location;
c) rotating the coil about the longitudinal axis to advance the coil into engagement with the first tissue location;
d) retracting the first tubular member to retract the first tissue location engaged by the coil; and
e) advancing the fastener at least partially through the coil and into the first tissue location.

29. The method according to claim 28, wherein:
the fastener is coupled to a suture that extends through the first tubular member, and after the fastener is advanced into the first tissue, the fastener rotates relative to the longitudinal axis on the suture.

30. The method according to claim 28, wherein:
the fastener deployment system houses a plurality of fasteners, and further comprising, for each fastener to be deployed,
positioning the distal end of the deployment system adjacent a respective tissue location
rotating the coil about the longitudinal axis to advance the coil into engagement with the respective tissue location;
retracting the first tubular member to retract the respective tissue location engaged by the coil; and
advancing the fastener at least partially through the coil and into the respective tissue location.

31. The method according to claim 30, wherein:
the plurality of fasteners are coupled to a common suture, and applying tension on the suture between the deployed fasteners to reconfigure the first and respective tissue locations relative to each other, and then retaining the applied tension to the suture.

32. A method of deploying fasteners into tissue of a patient, comprising:
a) providing a fastener deployment system having a proximal end and distal end, the deployment system including,
  i) a handle,
  ii) a flexible first tubular member having a proximal end and a distal end and defining a longitudinal axis, the proximal end rotatably coupled to the handle,
  iii) a flexible second tubular member having a proximal end and a distal end, and extending through the first flexible tubular member,
  iv) a fastener housing storing a plurality of tissue fasteners, the fastener housing provided at the distal end of the second tubular member and having a tissue-piercing distal tip, v) a coil having a tissue-piercing distal tip, the coil rotationally fixed relative to the distal end of the first tubular member, wherein rotation of the first tubular member relative to the handle results in rotation of the coil, and vi) a flexible push member longitudinally displaceable within the second tubular member and adapted to be axially displaced into the fastener housing;

b) piercing the tissue-piercing distal tip of the fastener housing through the first tissue location;

c) rotating the first tubular member to rotate the coil to advance the coil into engagement with the first tissue location;

d) retracting the first tubular member to retract the first tissue location engaged by the coil; and e) releasably deploying a first fastener at the first tissue location.

33. The method according to claim 32, wherein:
the first fastener is coupled to a suture that extends through the first tubular member.

34. The method according to claim 32, wherein:
after the first fastener is deployed at the first tissue location, the first fastener rotates relative to the longitudinal axis on the suture.

35. The method according to claim 32, further comprising:
providing an endoscope having a working channel, and the first and second tubular members, fastener housing, and coil of the deployment system are all advanced through the working channel prior to the piercing.

36. The method according to claim 35, wherein:
the endoscope is positioned within a natural body orifice.

37. The method according to claim 32, wherein:
prior to the piercing, the first fastener protrudes beyond the distal end of the fastener housing, and when the first fastener is pushed against tissue with a predetermined force, the first fastener is automatically retracted into the fastener housing to expose the distal end of the fastener housing.

38. The method according to claim 32, wherein:
prior to the rotating, the distal end of the fastener housing is pierced through the first tissue location no farther than the distal end of the coil.

39. The method according to claim 32, wherein:
the rotating the coil advances the needle housing through the first tissue location.

40. The method according to claim 32, wherein:
the deployment system further comprises an actuator movably coupled relative to the handle, wherein actuating the actuator once the results in longitudinal displacement of the push member relative to the first tubular member and into the fastener housing to release the first fastener.

41. The method according to claim 32, further comprising:
all without withdrawing the fastener deployment system from the patient,
moving the distal end of the deployment system from adjacent the first tissue location to adjacent a second tissue location;
piercing the tissue-piercing distal tip of the fastener housing through the second tissue location;
rotating the first tubular member to rotate the coil to advance the coil into engagement with the second tissue location;
retracting the first tubular member to retract the second tissue location engaged by the coil; and
releasably deploying a second fastener from the fastener housing at the second tissue location.

42. The method of claim 41, wherein:
the first and second fasteners are coupled to a suture that extends through the deployment system, further comprising,
applying tension to the suture to draw the first and second fasteners toward each other; and
retaining the applied tension on the suture.

43. The method of claim 42, wherein:
the applied tension is retained with a suture cinch.

44. The method of claim 41, wherein:
the first and second fasteners are coupled to a suture that extends through the deployment system, further comprising,
applying tension to the suture to draw the first and second tissue locations toward each other to reconfigure the tissue; and
retaining the applied tension on the suture.

45. The method of claim 44, wherein:
the first and second tissue locations are drawn into apposition.

* * * * *